United States Patent [19]
de Nanteuil et al.

[11] Patent Number: 5,296,605
[45] Date of Patent: Mar. 22, 1994

[54] 2,4-THIAZOLIDINEDIONE COMPOUNDS

[75] Inventors: Guillaume de Nanteuil, Suresnes; Jacques Duhault, Croissy sur Seine; Denis Ravel, Igny; Yolande Herve, Puteaux, all of France

[73] Assignee: Adir et Compagnie, Courbevoie, France

[21] Appl. No.: 11,268

[22] Filed: Jan. 29, 1993

Related U.S. Application Data

[62] Division of Ser. No. 930,001, Aug. 14, 1992, Pat. No. 5,266,582.

[30] Foreign Application Priority Data

Aug. 20, 1991 [FR] France ................... 91 10430

[51] Int. Cl.$^5$ .................. C07D 401/10; A61K 31/41
[52] U.S. Cl. ................................................ 546/176
[58] Field of Search .................. 546/176; 514/314

[56] References Cited

FOREIGN PATENT DOCUMENTS 8203 2/1980 European Pat. Off. .
207581 1/1987 European Pat. Off. .

*Primary Examiner*—David B. Springer
*Attorney, Agent, or Firm*—Gordon W. Hueschen

[57] ABSTRACT

Compounds of formula (I):

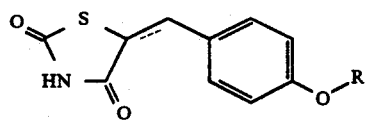

in which:
R represents any one of the groups defined in the description used as medicinal products.

5 Claims, No Drawings

2,4-THIAZOLIDINEDIONE COMPOUNDS

The present application is a division of our prior-filed copending application Ser. No. 07/930,001, filed Aug. 14, 1992, now U.S. Pat. No. 5,266,582.

The present invention relates to new 2,4-thiazolidinedione compounds.

Numerous 2,4-thiazolidinedione compounds have been described in the prior art as anti-diabetic agents. This is the case in particular for the compounds described in Patents EP 008203, WO 8607056, EP 207581 or WO 8504171.

However, the compounds of the present invention, in addition to the fact that they are new, differ from the other 2,4-thiazolidinedione compounds by the intensity of their pharmacological properties.

Indeed, insulin-resistance and a deficiency in insulin secretion are the causes of the glucose intolerance observed in patients having a non-insulin-dependent diabetes.

Currently available therapies essentially enable the deficiency in insulin secretion to be corrected without necessarily improving sensitivity of the peripheral tissues (muscles, adipose tissue) to insulin.

Compounds belonging to the 2,4-thiazolidinedione structure are capable of bringing about a reduction in glycemia and improving glucose tolerance in non-insulin-dependent diabetes models without bringing about an increase in insulin secretion. Our compounds possess the advantage of being particularly potent, more particularly relative to ciglitazone, a reference compound belonging to this chemical structure and whose efficacy remains low.

Accordingly, the compounds of the invention may be used in the treatment of non-insulinopenic diabetic states, enabling a better control of glycemia to be obtained while the level of insulin in circulation decreases. The prevention of this relative hyperinsulinemia, combined with a decrease in triglycerides in circulation under the effect of these products, may contribute to a reduction in the risks of macroangiopathy.

Furthermore, these same compounds are used in the treatment of hypertension in the elderly, who present an insulin-resistance combined or not with other metabolic disorders.

More specifically, the present invention relates to compounds of formula (I):

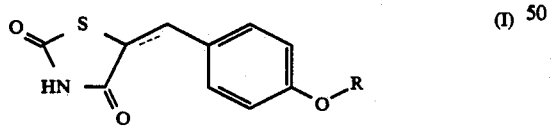

in which:
the dotted line indicates the presence or absence of a double bond,
R represents any one of the following groups:

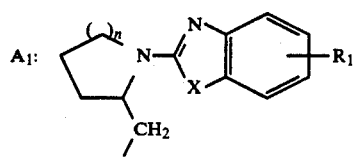

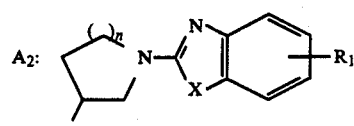

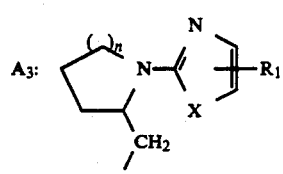

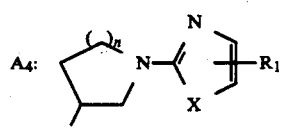

in which:
x represents a sulphur or oxygen atom or an NH radical which is unsubstituted or substituted by a linear or branched ($C_1$–$C_6$)alkyl group,
$R_1$ represents a hydrogen or halogen atom or a linear or branched ($C_1$–$C_6$)alkyl, linear or branched ($C_1$–$C_6$)alkoxy, trifluoromethyl or cyano group,
n is equal to 1, 2 or 3,

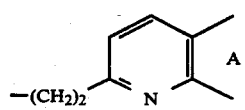

in which:
A represents an unsaturated or partially or completely saturated ring with 5 or 6 members,

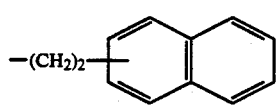

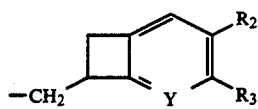

in which:
Y represents a nitrogen atom or a CH radical,
$R_2$ and $R_3$, which are identical or different, represent a hydrogen atom, a halogen atom, a linear or branched ($C_1$–$C_6$)alkyl group or a linear or branched ($C_1$–$C_6$)alkoxy group, or together form with the carbon atoms to which they are attached a saturated ring with 5 or 6 members which may contain 1 or 2 oxygen atoms,

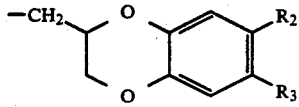

in which $R_2$ and $R_3$ are as defined above,

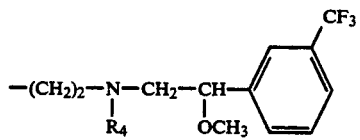 F in which:
$R_4$ represents a hydrogen atom or a linear or branched ($C_1$-$C_6$)alkyl group which is unsubstituted or substituted by a phenyl group,

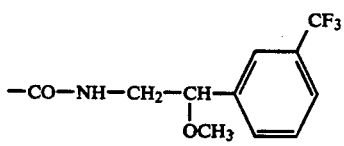 G

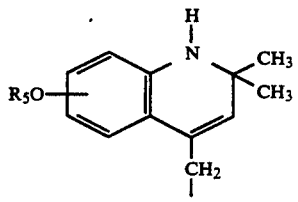 H in which:
$R_5$ represents a hydrogen atom or a linear or branched ($C_1$-$C_6$)alkyl group

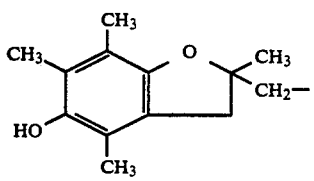 $J_1$

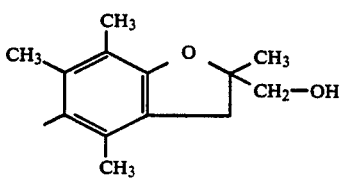 $J_2$

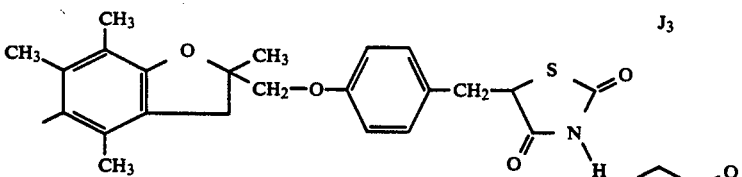 $J_3$ their enantiomers, diastereoisomers and epimers as well as their addition salts with a pharmaceutically acceptable acid.

Among the pharmaceutically acceptable acids, hydrochloric, sulfuric, tartaric, maleic, fumaric, methanesulfonic and camphoric acids and the like may be mentioned with no limitation being implied.

The invention also extends to the process for preparing the compounds of formula (I) wherein:
a either, in the case where the compounds of formula (I) which it is desired to obtain are such that R represents a group R' which is chosen from any one of the groups A to F and H, an alcohol of formula (II), in racemic or enantiomeric form,

 (II)

in which R' represents any one of the groups A to F, is reacted with para-hydroxybenzaldehyde of formula (III), according to a reaction described by Mitsunobu (Synthesis, 1981, 1):

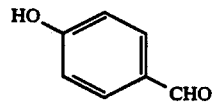 (III)

to give a compound of formula (IV):

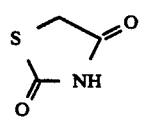 (V)

in which R' has the same meaning as above, which is subjected to the action of the 2,4-thiazolidinedione of formula (V), in the presence of a base such as piperidine:

(V)

to give a compound of formula (I/a), which is a specific example of the compounds of formula (I), (I/a)

in which R' has the same meaning as above, which compound is subjected, if desired, to catalytic hydrogenation in the presence of 10% palladium on carbon to give a compound of formula (I/b), which is a specific example of the compounds of formula (I),

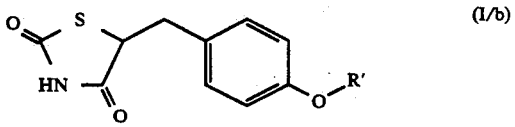
(I/b)

in which R' has the same meaning as above, b or, in the case where the compounds of formula (I) which it is desired to obtain are such that R represents a group R''=G, an amine of formula (VI);

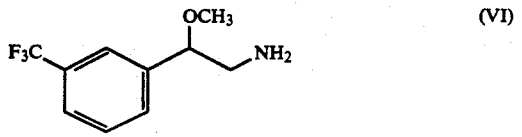
(VI)

is treated with excess phosgene, to give the corresponding isocyanate of formula (VII):

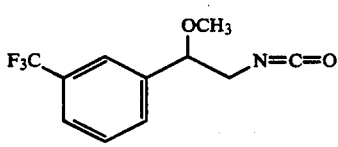
(VII)

which is reacted with the 2,4-thiazolidinedione of formula (VIII) which is described by KAWAMATSU et al. (Chem. Pharm. Bull. 1982, 3580),

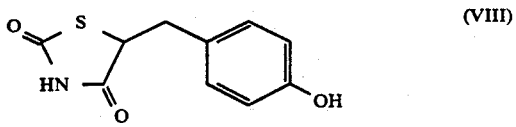
(VIII)

to give a compound of formula (I/c), which is a specific example of the compounds of formula (I),

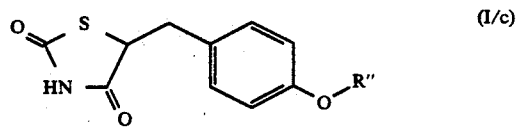
(I/c)

in which R'' has the same meaning as above, c or, in the case where the compounds of formula (I) which it is desired to obtain are such that R represents a group R''' which is chosen from any one of the groups $J_1$, $J_2$ or $J_3$, the compound of formula (IX), which is obtained according to the process described in Patent EP 0345593:

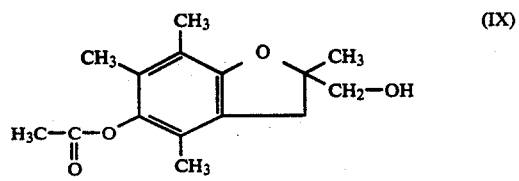
(IX)

is treated with sodium hydride and then with 4-fluoronitrobenzene, to give the compounds of formula (Xa), (Xb) and (Xc) in the form of a mixture:

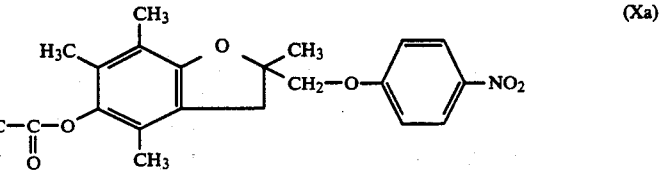
(Xa)

+

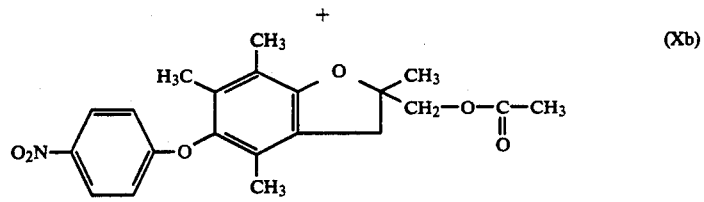
(Xb)

+

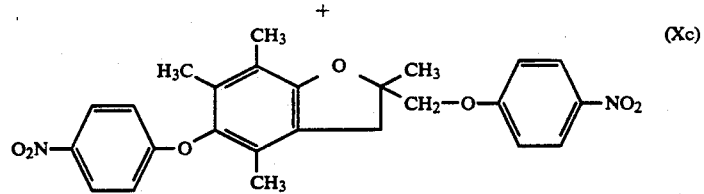
(Xc)

which mixture is subjected to purification by chromatography on a silica column enabling the compound of formula (Xc) to be separated from the (Xa)/(Xb) mixture: the mixture of compounds (Xa)/(Xb) is then subjected to catalytic hydrogenation resulting in the mixture of compounds (XIa)/(XIb):

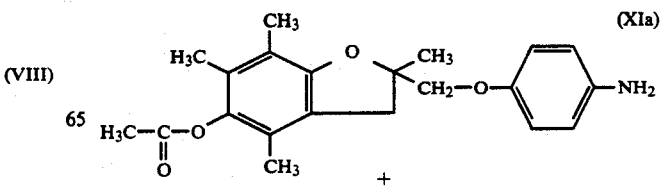
(XIa)

+

-continued

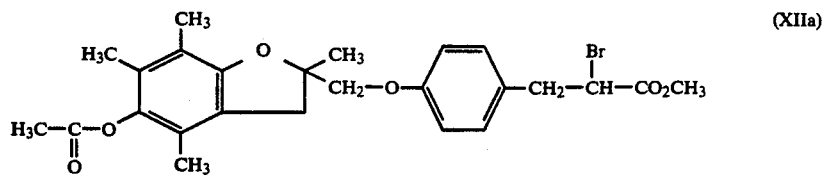 (XIb)

presence of copper(I) oxide, to give the compounds of formula (XIIA) and (XIIB) respectively:

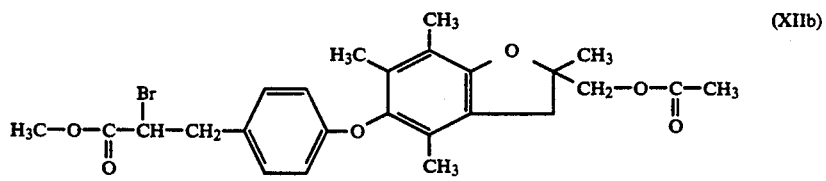 (XIIa)

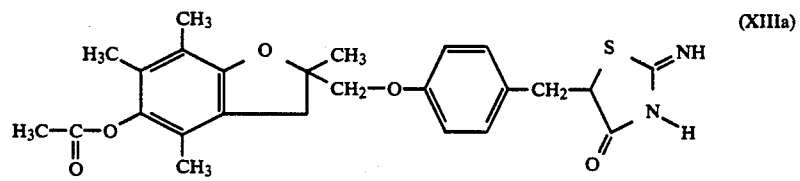 (XIIb)

which are reacted with thiourea in the presence of sodium acetate, to give the compounds of formula (XIIIA) and (XIIIB) respectively:

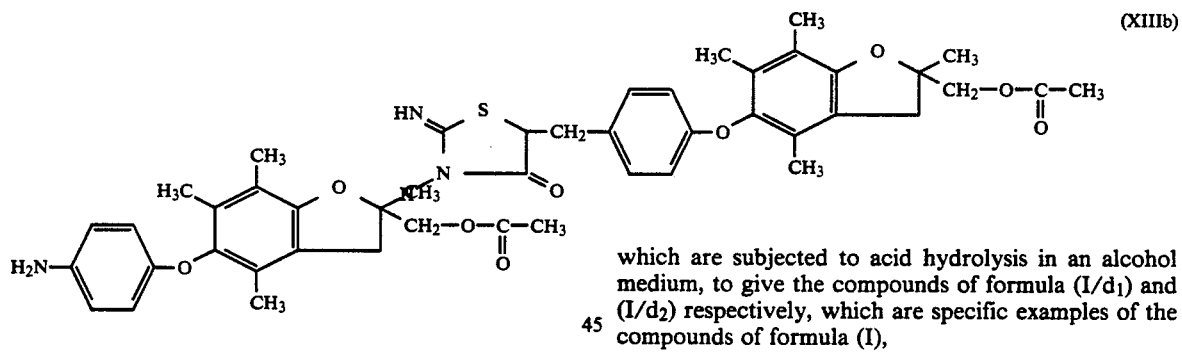

(XIIIa)

(XIIIb)

which are subjected to acid hydrolysis in an alcohol medium, to give the compounds of formula (I/d$_1$) and (I/d$_2$) respectively, which are specific examples of the compounds of formula (I),

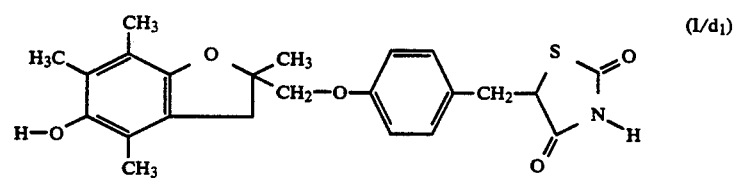 (I/d$_1$)

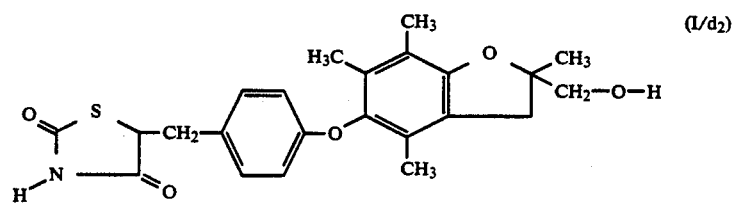 (I/d$_2$)

which are then separated by chromatography on a silica column, which compounds of formula (XIa) or (XIb) are reacted with hydrobromic acid in the presence of sodium nitrite and then with methyl acrylate in the which compound of formula (Xc) is subjected to catalytic hydrogenation to give the compound of formula (XIc):

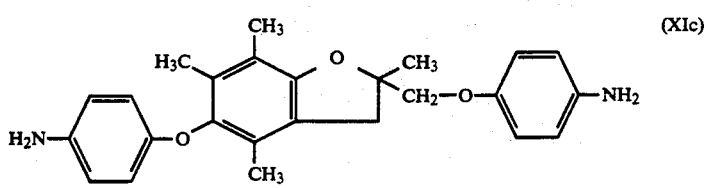
(XIc)

which is reacted with hydrobromic acid in the presence of sodium nitrite and then with methyl acrylate in the presence of copper(I) oxide, to give the compound of formula (XIIc);

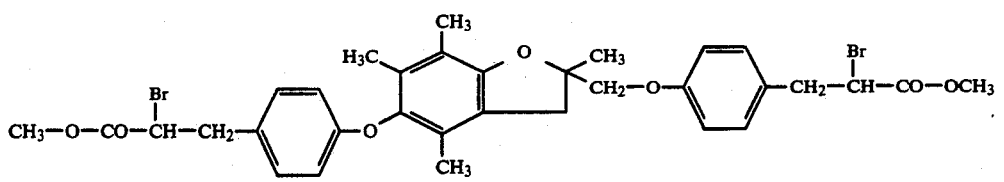
(XIIc)

which is reacted with thiourea in the presence of sodium acetate, to give a compound of formula (XIIIc):

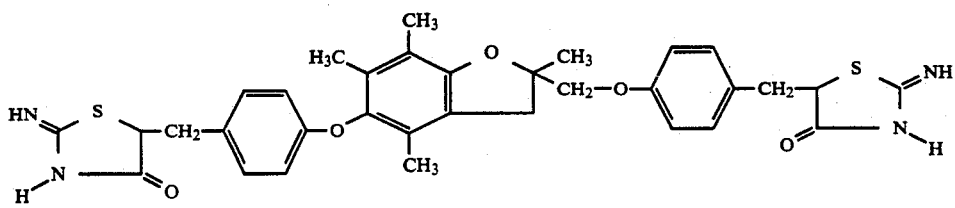
(XIIIc)

which is subjected to acid hydrolysis in an alcoholic medium, to give the compound of formula (I/d$_3$), which is a specific example of the compounds of formula (I):

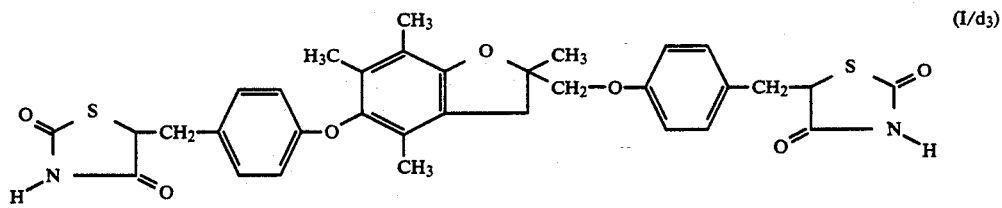
(I/d$_3$)

which compounds of formula (I/a), (I/b), (I/c), (I/d$_1$), (I/d$_2$) or (I/d$_3$) are purified, if appropriate, by a conventional purification technique, whose isomers are separated, if desired, according to a conventional separation technique and which are converted, if necessary, into their addition salts with a pharmaceutically acceptable acid.

The compounds of formula (I) possess very useful pharmacological properties. Thiazolidinedione compounds are generally inactive in vitro and in normoglycemic animals not exhibiting a glucose tolerance disorder. The pharmacological test of the compounds of the invention is therefore performed using a non-insulin-dependent diabetes model (NIDDM); ob/ob mice, and using a decreased glucose tolerance model which is associated with hyperinsulinemia and hyperlipemia : the Zucker FaFa rat. The results obtained during these tests show that the compounds of the invention permit control of glycemia while the levels of insulin in circulation and of triglycerides decrease.

In addition to these pharmacological properties relating to hyperinsulinemia, the compounds of formula (I), although lacking intrinsic hypotensive activity, decrease the blood pressure of insulin-resistant subjects and may therefore be used therapeutically, in the treatment of hypertension associated with insulin-resistant states and other metabolic diseases such as, for example, obesity, dyslipemia, hyperinsulinemia and the like, which constitute important cardiovascular risk factors (coronaropathies, macroangiopathy and the like).

The subject of the present invention is also pharmaceutical compositions containing, as active ingredient, at least one compound of general formula (I) or one of these addition salts with a pharmaceutically acceptable acid, either alone or in combination with one or more inert, nontoxic excipients or vehicles.

Among the pharmaceutical compositions according to the invention, there may be mentioned more particularly those which are suitable for oral, parenteral or nasal administration, ordinary or sugared tablets, sublingual tablets, sachets, packets, gelatin capsules, suppositories, creams, ointments, skin gels and the like.

The effective dosage varies according to the age and weight of the patient, the nature and seriousness of the affection as well as the route of administration. The latter may be oral, nasal, rectal or parenteral. In general, the unit dosage ranges between 50 and 1,000 mg for a treatment using 1 to 3 doses per 24 hours.

The following examples illustrate the invention and do not imply any limitation thereto.

EXAMPLE 1

(−)-5-{4-[1-(2-Benzothiazolyl)-(2S)-pyrrolidinyl]methoxy]benzylidene}-2,4-thiazolidinedione

STAGE A:
(S)-1-(Benzothiazolyl)-2-hydroxymethyl-pyrrolidine 15 g of (S)-(+)-2-pyrrolidinemethanol are placed, at room temperature, in 100 ml of anhydrous acetonitrile in the presence of 20.5 g of potassium carbonate and 25g of 2-chlorobenzothiazole.

This mixture is refluxed for 15 hours and then filtered and the solution is evaporated under vacuum.

The residue is taken up in 200 ml of 2N hydrochloric acid and the solution obtained is washed with ether.

The solid which precipitates from the acidic aqueous phase is filtered, washed with ether and dried. It is then dissolved in water and the solution is adjusted to pH 12 by means of concentrated sodium hydroxide.

The expected product is obtained after extraction with methylene chloride, drying and evaporation of the solvent.

Melting point: 1100° C.

STAGE B:
(S)-1-(2-Benzothiazolyl)-2-(4-formyl-phenoxymethyl)-pyrrolidine 119 g of ethyl azodicarboxylate are added dropwise, at 15° C., to 190 g of triphenylphosphine dissolved in 1.5 liters of tetrahydrofuran (THF).

After 5 minutes at room temperature, 44 g of parahydroxybenzaldehyde in 1.5 liters of THF are rapidly added dropwise, at room temperature, followed by 85 g of the product described in stage A, dissolved beforehand in 1.5 liters of THF.

After leaving overnight at room temperature, the solvent is evaporated. Part of the triphenylphosphine oxide formed crystallizes on triturating the residue with ether. The filtrate is concentrated and purified by chromatography on a silica gel using as eluent an ether/cyclohexane mixture: 80/20.

The solid compound obtained is filtered and thoroughly washed with ether. The filtrate is dried and evaporated and leads to the expected product in the form of an oil.

STAGE C:
(−)-5-{4-[[1-(2-Benzothiazolyl)-(2S)-2-pyrrolidinyl]methoxy]benzylidene}-2,4- thiazolidinedione 30 g of the compound obtained in stage B are placed, at room temperature, in 650 ml of ethanol in the presence of 10.3 g of thiazolidinedione and 6 ml of piperidine. The mixture is refluxed for 24 hours. The expected product precipitates on cooling, and it is filtered and washed with isopropanol and ether.

Melting point: 192°–194° C.

|  | Elemental microanalysis: | | | |
| --- | --- | --- | --- | --- |
|  | C % | H % | N % | S % |
| Calculated | 60.39 | 4.38 | 9.60 | 14.66 |
| Found | 60.38 | 4.33 | 9.62 | 13.66 |

EXAMPLE 2

(+)-5-(4-[[1-(2-Benzothiazolyl)-(2R)-2-pyrrolidinyl]methoxylbenzylidene)-2,4-thiazolidinedione

STAGE A:
(R)-1-(2-benzothiazolyl)-2-hydroxymethyl-pyrrolidine

The expected product is obtained by carrying out the procedure as in stage A of Example 1, but replacing (S)-(+)-2-pyrrolidinemethanol with R-(-)-2-pyrrolidinemethanol.

Melting point: 110° C.

STAGE B:
(R)-1-(2-Benzothiazolyl)-2-(4-formylphenoxymethyl)-pyrrolidine

This stage is identical to stage B of Example 1.

STAGE C:
(+)-5-(4-([1-(2-Benzothiazolyl)-(2R)-2-pyrrolidinyl]-methoxylbenzylidene)-2,4- thiazolidinedione This stage is identical to stage C of Example 1.
Melting point: 214°–215° C.

|  | Elemental microanalysis: | | | |
| --- | --- | --- | --- | --- |
|  | C % | H % | N % | S % |
| Calculated | 60.39 | 4.38 | 9.60 | 14.66 |
| Found | 60.02 | 4.34 | 9.76 | 14.57 |

EXAMPLE 3

(−)-5-{4-[[1-(2-Benzoxazolyl)-(2S)-2-pyrrolidinyl]methoxy]benzylidene}-2,4-thiazolidinedione

STAGE A:
(S)-1-(2-Benzoxazolyl)-2-hydroxymethylpyrrolidine

The expected product is obtained by carrying out the procedure as in stage A of Example 1 but replacing 2-chlorobenzothiazole with 2-chlorobenzoxazole.

Melting point: 88° C.

STAGE B: (S)-1-( 2-Benzoxazolyl )-2-( 4-formyl-phenoxymethyl)pyrrolidine

This stage is identical to stage B of Example 1.

STAGE C: (−)-5-[4-[[1-(2-Benzoxazolyl)-(2S)-2-pyrrolidinyl]methoxy]benzylidene}-2,4-thiazolidinedione This stage is identical with stage C of Example 1.
Melting point: 214° C.

|  | Elemental microanalysis: | | | |
| --- | --- | --- | --- | --- |
|  | C % | H % | N % | S % |
| Calculated | 62.69 | 4.69 | 10.21 | 7.61 |
| Found | 62.69 | 4.75 | 10.21 | 7.47 |

EXAMPLE 4

5-{4-[(2-Benzodioxanyl)methoxy]benzylidene]-2,4-thiazolidinedione

STAGE A: 2-(4-Formylphenoxymethyl)benzodioxane

The expected product is obtained by carrying out the procedure as in stage B of Example 1 but replacing the product described in stage A with 2-hydroxymethyl-benzodioxane.
Melting point: 67° C.

STAGE B:
5-[4-[(2-Benzodioxanyl)methoxy]benzylidenel-2,4-thiazolidinedione

This stage is identical to stage C of Example 1.
Melting point: 227°–228° C.

|  | Elemental microanalysis: | | | |
|---|---|---|---|---|
|  | C % | H % | N % | S % |
| Calculated | 61.78 | 4.09 | 3.79 | 8.68 |
| Found | 61.71 | 4.28 | 4.00 | 8.83 |

EXAMPLE 5

5-[4-[(1-Benzocyclobutanyl)-methoxylbenzylidene]-2,4-thiazolidinedione

STAGE A:
1-(4-Formylphenoxymethyl)benzocyclobutane

The expected product is obtained by carrying out the procedure as in stage B of Example 1, but replacing the product described in stage A with 1-hydroxymethyl-benzocyclobutane.
Melting point: 52° C.

STAGE B:
5-[4-[(1-Benzocyclobutanyl)methoxy]benzylidene]-2,4-thiazolidinedione

This stage is identical to stage C of Example 1.
Melting point: 195° C.

|  | Elemental microanalysis: | | | |
|---|---|---|---|---|
|  | C % | H % | N % | S % |
| Calculated | 67.64 | 4.48 | 4.15 | 9.50 |
| Found | 67.32 | 4.65 | 4.39 | 9.52 |

EXAMPLE 6

5-[4-[(4,5-Methylenedioxybenzocyclobutan-1-yl)methoxylbenzylidenel-2,4-thiazolidinedione STAGE A:
1-(4-Formylphenoxymethyl)-4,5-methylenedioxybenzocyclobutane The expected product is obtained by carrying out the procedure as in stage B of Example 1, but replacing the product described in stage A with 1-hydroxymethyl-4,5-methylenedioxybenzocyclobutane.
Melting point: [lacuna]

STAGE B: 5-[4-4,5-Methylenedioxybenzocyclobutan-1-yl)methoxylbenzylidenel-2,4-thiazolidinedione This stage is identical to stage C of Example 1.
Melting point: 205°–208° C.

|  | Elemental microanalysis: | | | |
|---|---|---|---|---|
|  | C % | H % | N % | S % |
| Calculated | 62.98 | 3.96 | 3.67 | 8.41 |
| Found | 63.40 | 4.10 | 3.79 | 8.38 |

EXAMPLE 7

5-[4-[2-(2-Naphthyl)ethoxy]bnenzylidene]-2,4-thiazolidinedione

STAGE A: 2-(4-Formylphenoxyethyl)naphthalene

The expected product is obtained by carrying out the procedure as in stage B of Example 1, but replacing the product described in stage A with 2-naphthalene ethanol.
Melting point: 64°–65° C.

STAGE B:
5-[4-[2-(2-Naphthyl)ethoxylbenzylidenel-2,4-thiazolidinedione

This stage is identical to stage C of Example 1.
Melting point: 171°–1730° C.

|  | Elemental microanalysis: | | | |
|---|---|---|---|---|
|  | C % | H % | N % | S % |
| Calculated | 70.38 | 4.56 | 3.73 | 8.54 |
| Found | 70.15 | 4.63 | 4.02 | 7.93 |

EXAMPLE 8

5[4-[2-(1-Naphthyl)ethoxylbenzylidenel-2,4-thiazolidinedione

STAGE A: 1-(4-Formylphenoxyethyl)naphthalene

The expected product is obtained by carrying out the procedure as in stage B of Example 1, but replacing the product described in stage A with 1-naphthalene ethanol.

STAGE B: 5-( 4- [2- ( 1-Naphthy 1 ) et hoxy ]benzyl idene)-2 4-thiazolidinedione This stage is identical to stage C of Example 1.
Melting point ; 229° C.

|  | Elemental microanalysis: | | | |
|---|---|---|---|---|
|  | C % | H % | N % | S % |
| Calculated | 70.38 | 4.56 | 3.73 | 8.54 |
| Found | 70.59 | 4.66 | 3.82 | 8.24 |

EXAMPLE 9

5-[4-[2-(2-Quinolyl)ethoxylbenzylidenel-2,4-thiazolidinedione

STAGE A: 2-(4-Formylphenoxyethyl)quinoline

STAGE B:
5-[4-[2-(2-Quinolyl)ethoxy]benzylidene]-2,4-thiazolidinedione

EXAMPLE 10

5-[4-[2-(5,6,7,8-Tetrahydroquinol-2-yl)ethoxy]benzylidene]-2,4-thiazolidinedione

STAGE A: 2-(4-Formylphenoxyethyl)-5,6,7,8-tetrahydroquinoline

STAGE B:
5-[4-[2-(5,6,7,8-Tetrahydroquinol-2-yl)ethoxylbenzylidene]-2,4-thiazolidinedione

EXAMPLE 11

(−)-5-(4-[[1-(6-Chlorobenzothiazol-2-yl)-(2S)-2-pyrrolidinyl]methoxy]benzylidene]-2,4-thiazolidinedione

STAGE A:
(S)-1-(6-Chlorobenzothiazol-2-yl)-2-hydroxymethylpyrrolidine

STAGE B:
(S)-1-(6-Chlorobenzothiazol-2-yl)-2-(4-formylphenoxymethyl)pyrrolidine

STAGE C:
(−)-5-(4-[[1-(6-chlorobenzothiazol-2-yl)-(2S)-2-pyrrolidinyl]methoxylbenzylidene)-2,4-thiazolidinedione

EXAMPLE 12

(−)-5-{4-[[1-(2-Thiazolyl)-(2S)-2-pyrrolidinyl]methoxy]benzylidene}-2,4-thiazolidinedione

STAGE A:
(S)-1-(2-Thiazolyl)-2-hydroxymethylpyrrolidine

STAGE B:
(S)-1-(2-Thiazoyly)-2-(4-formylphenoxymethyl)pyrrolidine

STAGE C:
(−)-5-{4-[[1-(2-thiazoyly)-(2S)-2-pyrrolidinyl]methoxy]benzylidene}-2,4-thiazolidinedione

EXAMPLE 13

5-{4-[[1-(2-Benzothiazolyl)-3-pyrrolidinyl]oxy]benzylidene]-2,4-thiazolidinedione STAGE A: 1-(2-Benzothiazolyl)-3-hydroxypyrrolidine

STAGE B:
1-(2-Benzothiazolyl)-3-(4-formylphenoxy)pyrrolidine

STAGE C:
5-{4-[[1-(2-Benzothiazoyly)-3-pyrrolidinyl]oxy]benzylidene]-2,4-thiazolidinedione

EXAMPLE 14

5-{4-[[2-(3-Trifluoromethylphenyl)-2-(methoxy)ethylamino]ethoxy]benzylidene]- 2,4-thiazolidinedione

EXAMPLE 15

(−)-5-{4-[[l-(2-Benzothiazolyl)-(2S)-2-pyrrolidinyl]methoxylbenzyl}-2,4- thiazolidinedione The compound described in Example 1 is hydrogenated in dioxane at 80°-100°, at 60-80 kg, for 24 hours, in the presence of 10 % palladized carbon.

The reaction is continued until the starting product disappears.

The expected product is obtained after filtration of the catalyst.

Melting point: 950° C.

| | Elemental microanalysis: | | | |
|---|---|---|---|---|
| | C % | H % | N % | S % |
| Calculated | 60.12 | 4.82 | 9.56 | 14.59 |
| Found | 59.34 | 5.15 | 9.43 | 14.17 |
| Specific rotation: $[\alpha]_D^{20}$ = −99.0° (c = 10 mg/ml, DMSO) | | | | |

EXAMPLE 16

(+)-5-{4-[[1-(2-Benzothiazolyl)-(2R)-2-pyrrolidinyl]methoxylbenzyl)-2,4- thiazolidinedione The expected product is obtained by carrying out the procedure as in Example 15 but hydrogenating the compound described in Example 2.

Melting point ; 94.6° C.

| | Elemental microanalysis: | | | |
|---|---|---|---|---|
| | C % | H % | N % | S % |
| Calculated | 60.12 | 4.82 | 9.56 | 14.59 |
| Found | 60.79 | 4.91 | 9.56 | 13.94 |
| Specific rotation: $[\alpha]_D^{20}$ = +105.4° (c = 10 mg/ml, DMSO) | | | | |

EXAMPLE 17

(−)-5-{4-[[1-(2-Benzoxazolyl)-(2S)-2-pyrrolidinyl]methoxy]benzyl}-2,4-thiazolidinedione The expected product is obtained by carrying out the procedure as in Example 15 but hydrogenating the compound described in Example 3.

Melting point: 95°-107° C.

| | Elemental microanalysis: | | | |
|---|---|---|---|---|
| | C % | H % | N % | S % |
| Calculated | 62.40 | 5.00 | 9.92 | 7.57 |
| Found | 62.44 | 5.31 | 10.04 | 7.36 |
| Specific rotation: $[\alpha]_D^{20}$ = −116.7° (c = 10 mg/ml, DMSO) | | | | |

EXAMPLE 18

5-[4-(Benzodioxanyl)methoxybenzyl]-2,4-thiazolidinedione

The expected product is obtained by carrying out the procedure as in Example 15 but hydrogenating the compound described in Example 4.

Melting point: 157°-159° C.

| | Elemental microanalysis: | | | |
|---|---|---|---|---|
| | C % | H % | N % | S % |
| Calculated | 61.44 | 4.61 | 3.77 | 8.63 |
| Found | 61.12 | 4.79 | 4.17 | 8.48 |

EXAMPLE 19

5-[4-(1-Benzocyclobutanyl)methoxylbenzyl-2,4-thiazolidinedione

The expected product is obtained by carrying out the procedure as in Example 15 but hydrogenating the compound described in Example 5.
Melting point: 101°-102° C.

| | Elemental microanalysis: | | | |
|---|---|---|---|---|
| | C % | H % | N % | S % |
| Calculated | 67.24 | 5.05 | 4.13 | 9.45 |
| Found | 67.01 | 5.24 | 4.33 | 9.30 |

EXAMPLE 20

5-[4-[(4,5-Methylenedioxybenzocyclobutane-1-yl)methoxylbenzyl]2,4-thiazolidinedione The expected product is obtained by carrying out the procedure as in Example 15 but hydrogenating the compound described in Example 6.
Melting point: 134°-138° C.

| | Elemental microanalysis: | | | |
|---|---|---|---|---|
| | C % | H % | N % | S % |
| Calculated | 62.65 | 4.47 | 3.65 | 8.36 |
| Found | 62.91 | 4.71 | 3.73 | 8.30 |

EXAMPLE 21

5-[4-12-(Naphthyl)ethoxylbenzyl]-2,4-thiazolidinedione

The expected product is obtained by carrying out the procedure as in Example 15 but hydrogenating the compound described in Example 7.
Melting point: 111° C.

| | Elemental microanalysis: | | | |
|---|---|---|---|---|
| | C % | H % | N % | S % |
| Calculated | 70.01 | 5.07 | 3.71 | 8.49 |
| Found | 69.55 | 5.24 | 3.96 | 8.64 |

EXAMPLE 22

5-[4-[2-(1-Naphthyl)ethoxylbenzyl]-2,4-thiazolidinedione

The expected product is obtained by carrying out the procedure as in Example 15 but hydrogenating the compound described in Example 8.
Melting point 121°-122° C.

| | Elemental microanalysis: | | | |
|---|---|---|---|---|
| | C % | H % | N % | S % |
| Calculated | 70.01 | 5.07 | 3.71 | 8.49 |
| Found | 70.50 | 5.48 | 3.78 | 8.19 |

EXAMPLE 23

5-[4-[2-(2-Quinolyl)ethoxy]benzyl]-2,4-thiazolidinedione

The expected product is obtained by carrying out the procedure as in Example 15 but hydrogenating the compound described in Example 9.

EXAMPLE 24

5-[4-[2-(5,6,7,8-Tetrahydroquinol-2-yl)ethoxylbenzyl]-2,4-thiazolidinedione

The expected product is obtained by carrying out the procedure as in Example 15 but hydrogenating the compound described in Example 10.

EXAMPLE 25

(−)-5-{4-[[1-(6-Chlorobenzothiazol-2-yl)-(2S)-2-pyrrolidinyl]methoxylbenzyl}-2,4-thiazolidinedione The expected product is obtained by carrying out the procedure as in Example 15 but hydrogenating the compound described in Example 11.

EXAMPLE 26

(−)-5-f4-[[1-(2-Thiazolyl)-(2S)-2-pyrrolidinyl]methoxylbenzyl)-2,4- thiazolidinedione The expected product is obtained by carrying out the procedure as in Example 15 but hydrogenating the compound described in Example 12.

EXAMPLE 27

5-{4[[1-(2-Benzothiazolyl)-3-pyrrolidinyl]oxylbenzyl)-2,4- thiazolidinedione

The expected product is obtained by carrying out the procedure as in Example 15 but hydrogenating the compound described in Example 13.

EXAMPLE 28

5-{4-[[2-(3-Trifluoromethylphenyl)-2-(methoxy)ethylaminolethoxylbenzyl)-2,4-thiazolidinedione The expected product is obtained by carrying out the procedure as in Example 15 but hydrogenating the compound described in Example 14.

EXAMPLE 29

5-[4-[2-(3-Trifluoromethylphenyl)-2-(methoxy)ethylaminocarbonyloxylbenzyll- 2,4-thiazolidinedione

STAGE A:
2-(3-Trifluoromethylphenyl)-2-(methoxy)ethylisocyanate

A solution containing 1 g of 2(3-trifluoromethylphenyl)-2-(methoxy)ethylamine in solution in 10 ml of toluene is added, at 5°-10° C., to a solution containing 2.3 g of phosgene in 10 ml of toluene.
The mixture is refluxed for 1 hour. The expected product is obtained in the form of a colorless oil and is purified by distillation.
b.p. = 120°-130° C. (p=15 Mm/Hg)

STAGE B:
5-[4-[2-(3-Trifluoromethylphenyl)-2-(methoxy)ethylaminocarbonyloxylbenzyll-2,4-thiazolidinedione A solution containing 1.5 g of the compound prepared in stage A in 10 ml of benzene is added to a solution containing 1.4 g of 5-[(4-hydroxyphenyl)methyll-2,4-thiazolidinedione in 5 ml of tetrahydrofuran.
The mixture is refluxed overnight. After evaporation of the solvents, the residue is triturated with ether and leads to the expected product.
Melting point: 58°-60° C.

| Elemental microanalysis: | | | | |
|---|---|---|---|---|
| | C % | H % | N % | S % |
| Calculated | 53.96 | 3.88 | 5.99 | 6.86 |
| Found | 53.89 | 4.04 | 6.14 | 6.55 |

EXAMPLE 30

5-[4-[(4,5-Dimethoxybenzocyclobutan-1-yl)methoxyl-benzylidenej-2,4- thiazolidinedione STAGE A;
1-(4-Formylphenoxymethyl)-4,5-dimethoxybenzocyclobutane The expected product is obtained by carrying out the procedure as in stage B of Example 1 but replacing the product described in stage A with 1-hydroxymethyl-4,5-dimethoxyebenzocyclobutane.

STAGE B:
5-[4-[(4,5-Dimethoxybenzocyclobutanyl)methoxyl-benzylidenel-2,4-thiazolidinedione This stage is identical to stage C of Example 1.

| Elemental microanalysis: | | | | |
|---|---|---|---|---|
| | C % | H % | N % | S % |
| Calculated | 63.46 | 4.82 | 3.52 | 8.07 |
| Found | 62.78 | 5.28 | 3.54 | 7.69 |

EXAMPLE 31

5-[4-[(4,5-Ethylenedioxybenzocyclobutan-1-yl)methoxy]benzylidenel-2,4- thiazolidinedione STAGE A:
1-(4-Formylphenoxymethyl)-4,5-ethylenedioxybenzocyclobutane The expected product is obtained by carrying out the procedure as in stage B of Example 1 but replacing the product described in stage A with 1-hydroxymethyl-4,5-ethylenedioxybenzocyclobutane.

STAGE B:
5-[4-[(4,5-Ethylenedioxybenzocyclobutan-1-yl)methoxylbenzylidenej-2,4-thiazolidinedione This stage is identical to stage C of Example 1.

| Elemental microanalysis: | | | | |
|---|---|---|---|---|
| | C % | H % | N % | S % |
| Calculated | 63.79 | 4.33 | 3.54 | 8.11 |
| Found | 64.45 | 4.80 | 3.59 | 7.85 |

EXAMPLE 32

5-[4-[(4,5-Dimethoxybenzocyclobutan-1-yl)methoxyl-benzylj-2,4-thiazolidinedione

The expected product is obtained by carrying out the procedure as in Example 15 but hydrogenating the compound described in Example 30.

| Elemental microanalysis: | | | | |
|---|---|---|---|---|
| | C % | H % | N % | S % |
| Calculated | 63.14 | 5.30 | 3.51 | 8.03 |

| Elemental microanalysis: | | | | |
|---|---|---|---|---|
| | C % | H % | N % | S % |
| Found | 62.69 | 5.46 | 3.56 | 7.54 |

EXAMPLE 33

5-[4-[(4,5-Ethylenedioxybenzocyclobutan-1-yl)methoxylbenzyll-2,4-thiazolidinedione The expected product is obtained by carrying out the procedure as in Example 15 but hydrogenating the compound described in Example 31.

| Elemental microanalysis: | | | | |
|---|---|---|---|---|
| | C % | H % | N % | S % |
| Calculated | 63.46 | 4.82 | 3.52 | 8.07 |
| Found | 63.89 | 5.24 | 3.68 | 8.39 |

EXAMPLE 34

5-[4-[(6-Ethoxy-1,2-dihydro-2,2-dimethylquinol-4-yl)methoxylbenzyll-2,4-thiazolidinedione, hydrochloride STAGE A:
4-(4-Formylphenoxymethyl)-6-ethoxy-1,2-dihydro-2,2-dimethylquinoline The expected product is obtained by carrying out the procedure as in stage B of Example 1 but replacing the product described in stage A with 4-hydroxymethyl-6-ethoxy-1,2-dihydro -2,2-dimethylquinoline.

STAGE B: 5-[4[(6-Ethoxy-1,2-dihydro-2,2-dimethylquinol- 4-yl)methoxylbenzylidenel-2,4- thiazolidinedione, hydrochloride This stage is identical to stage C of Example 1.

STAGE C: 5-[4[(6-Ethoxy-1,2-dihydro-2,2-dimethylquinol-4-yl)methoxylbenzyll-2,4-thiazolidinedione, hydrochloride The expected product is obtained by carrying out the procedure as in Example 15 using the compound obtained in stage B as starting material, and it is converted to the hydrochloride by means of hydrochloric ether.

Melting point: 155° C.

| Elemental microanalysis: | | | | | |
|---|---|---|---|---|---|
| | C % | H % | N % | S % | Cl % |
| Calculated | 60.69 | 5.73 | 5.90 | 6.75 | 7.46 |
| Found | 60.97 | 6.06 | 6.01 | 6.52 | 7.43 |

EXAMPLES 35, 36 and 37

EXAMPLE 35

5-[4-[(2,3-Dihydro-5-hydroxy-2,4,6,7-tetramethylbenzofuran-2-yl)methoxy]benzyl]-2,4-thiazolidinedione

EXAMPLE 36

5-[4[(2,3-Dihydro-2-hydroxymethyl-2,4,6,7-tetramethylbenzofuran-5-yloxylbenzyll- 2,4-thiazolidinedione

EXAMPLE 37

5-(4-[[2,3-Dihydro-2,4,6,7-tetramethyl-5-(4-((2,4-thiazolidinedione-5-yl)methyl)phenoxy)-2-benzofuranyl]methoxylbenzyl)- 2,4-thiazolidinedione Preparation A is the same for producing the compounds of Examples 35, 36 and 37. Preparations B and B' lead to intermediates which are useful in the synthesis of the compounds of Examples 35, 36 and 37.

PREPARATION A:

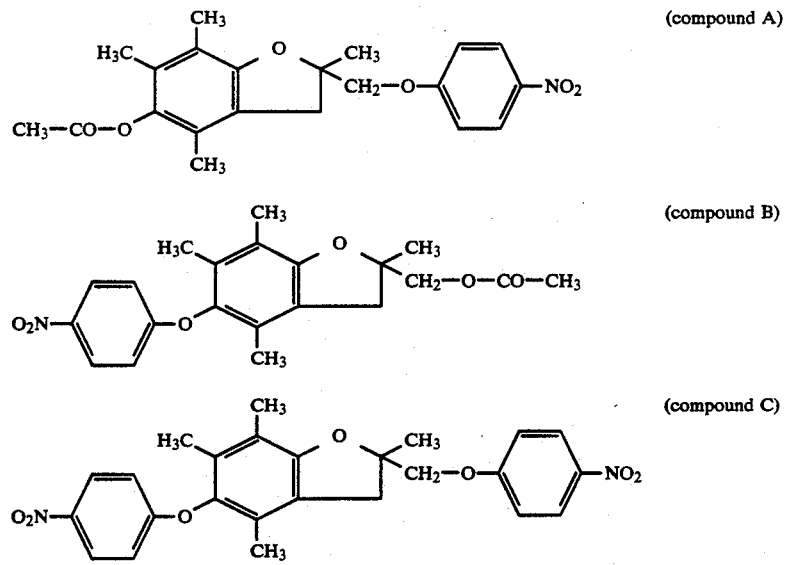

51 mmol of 2,3-dihydro-2,4,6,7-tetramethyl-2-hydroxymethyl-5-acetoxybenzofuran, prepared according to the procedure described in Patent EP 0,345,593, are dissolved in 200 ml of dimethylformamide. 51 mmol of para-fluoronitrobenzene are then added and the mixture is cooled to 10° C. under an inert atmosphere. 1,42 g of sodium hydride are slowly added. The mixture is left for 30 minutes at 5° C. and then for 2 hours at room temperature. After evaporation of the solvent the residue is taken up in 600 ml of ethyl acetate and the organic phase is successively washed with water, 0.5 N hydrochloric acid and then with a saturated solution of sodium chloride. After drying and evaporation, the crude residue containing the mixture of products A, B and C is purified by chromatography on a silica column using as eluent a dichloromethane/pentane mixture (1/1) followed by a dichloromethane/pentane mixture (7/3). This purification also enables compound C (2.8 g) to be separated from the mixture of compounds A and B (8.8 g).

PREPARATION B:

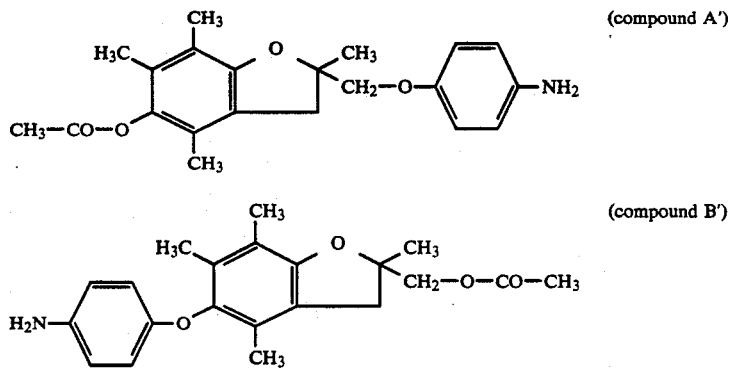

The mixture of compounds A and B obtained in the preceding stage, dissolved in an ethyl acetate/methanol mixture (5/2) is hydrogenolyzed for 5 hours 30 minutes, at atmospheric pressure, using palladium/C as catalyst.

After filtration of the catalyst and evaporation, the residual oil is purified by chromatography on a silica column using as eluent a butyl acetate/cyclohexane mixture (⅓ followed by ½). This purification enables compound A' to be separated from compound B'.

PREPARATION B':

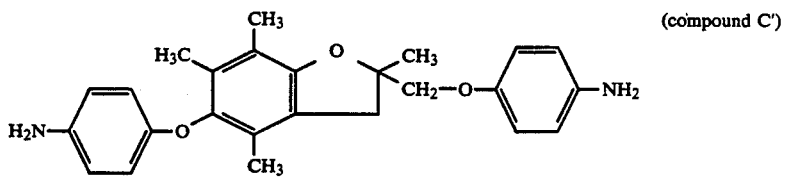

(compound C')

The hydrogenolysis which is performed under the same conditions as those described in preparation B, enables compound C' to be isolated.

EXAMPLE 35

5-[4-(2,3-Dihydro-5-hydroxy-2, 4, 6 7-tetramethylbenzofuran-2-yl)methoxy]benzyl]-2,4-thiazolidinedione

STAGE A:

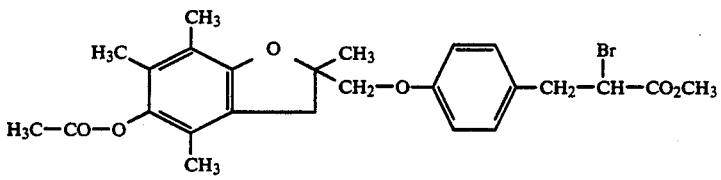

7.7 ml of a 45 % solution of hydrobromic acid in water are added to a solution, at 50C., containing 15 mmol of compound A', which is obtained in preparation B, in 15 ml of acetone and 15 ml of methanol, followed dropwise by 3 ml of an aqueous solution containing 1.18 g of sodium nitrite. After stirring for 15 minutes at 0° C. and adding methyl acrylate, the mixture is placed in a bath at 40° C. 343 mg of copper(I) oxide are then added and the temperature is maintained at 40° C. for 80 minutes. After evaporation, the residue is diluted with water. This aqueous phase is alkalized to pH=10 with concentrated ammonium hydroxide. The expected product is then extracted with ethyl acetate and purified, after evaporation, by chromatography on a silica column using as solvent a pentane/ethyl acetate mixture (85/15).

STAGE B:

5-[4[(2,3-dihydro-5-acetoxy-2,4,6,7-tetramethylbenzofuran-2-yl)methoxylbenzylj-2-imino-2,4-thiazolidinedione 6.14 mmol of the compound obtained in the preceding stage, 6.14 mmol of thiourea and 6.14 mmol of anhydrous sodium acetate in 60 ml of ethanol are refluxed for 13 hours. After evaporation, the residue is taken up in ethyl acetate. This organic phase is washed, dried and evaporated, and it leads to the expected product.
Melting point: 220° C.

STAGE C:

5-[4-[(2,3-Dihydro-5-hydroxy-2,4,6,7-tetramethylbenzofuran-2-yl)methoxylbenzylI-2,4-thiazolidinedione 5.5 mmol of the compound obtained in the preceding stage are dissolved in a mixture containing 25 ml of ethanol and 25 ml of 2N hydrochloric acid. The mixture is refluxed for 13 hours, evaporated to dryness and then taken up in ethyl acetate. This organic phase is washed, dried and evaporated, and it leads to the expected product which is purified by chromatography on a silica gel using as eluent a dichloromethane/ethyl acetate mixture (95/5).
Melting point: 134°-136° C.

| | Elemental microanalysis: | | | |
|---|---|---|---|---|
| | C % | H % | N % | S % |
| Calculated | 64.62 | 5.89 | 3.28 | 7.50 |
| Found | 64.00 | 6.21 | 3.30 | 6.54 |

EXAMPLE 36

5-14-1(2,3-Dihydro-2-hydroxymethyl-2,4,6,7-tetramethylbenzofuran-5-yloxylbenzyl]-2,4-thiazolidinedione The expected product is obtained according to the same procedure as that described in Example 35 using as starting product compound B' described in preparation B.
Melting point: 178°-179° C.

| | Elemental microanalysis: | | | |
|---|---|---|---|---|
| | C % | H % | N % | S % |
| Calculated | 64.62 | 5.89 | 3.28 | 7.50 |
| Found | 64.60 | 6.00 | 3.52 | 7.31 |

EXAMPLE 37

5-f4-[[2,3-Dihydro-2,4,6,7-tetramethyl-5-(4-((2,4-thiazolidinedione-5-yl)methyl)phenoxy)-2-benzofuranyllmethoxylbenzyl)- 2,4-thiazolidinedione The expected product obtained according to the same procedure as that described in Example 35 using as starting product compound C' described in preparation B'.
Melting point: 211°-213° C.

| | Elemental microanalysis: | | | |
|---|---|---|---|---|
| | C % | H % | N % | S % |
| Calculated | 62.64 | 5.10 | 4.43 | 10.13 |
| Found | 62.40 | 5.34 | 4.66 | 9.99 |

PHARMACOLOGICAL STUDY OF THE COMPOUNDS OF THE INVENTION

EXAMPLE 38

Study of the activity of the compounds of the invention using a non-insulin-dependent diabetes model (NIDDM)

The animals (ob/ob mice) are treated daily, for 4 days, by orally administering the compounds of the invention in suspension in a solution containing 20 % of Senegal gum.

On the 5th day, blood is collected by puncture of the orbital sinus and glycemia is determined. The reference compounds used are ciglitazone and compound CS045 (San Kyo).

Under these conditions, the compounds of the have a hypoglycemic power which is 5 to 20 times higher than that of ciglitazone and 2 to 10 times higher than compound CS045.

The table below gives the results for doses to be administered which cause the same hypoglycemic effect for the compounds of the invention and the reference compounds:

| Example | Dose (mg/kg/day) |
|---|---|
| 3 | 10 |
| 4 | 20 |
| 5 | 10 |
| 7 | 10 |
| 8 | 20 |
| 15 | 5 |
| 16 | 20 |
| 17 | 20 |
| 18 | 20 |
| 19 | 10 |
| 20 | 10 |
| 21 | 10 |
| 22 | 10 |
| 32 | 20 |
| 33 | 20 |
| 34 | 20 |
| 35 | 20 |
| 36 | 20 |
| 37 | 20 |
| ciglitazone | 100 |
| CS045 | 50 |

EXAMPLE 39

Study of the activity of the compounds of the invention using a decreased glucose tolerance model associated with hyperinsulinemia and hyperlipemia The animals (male Zucker Fa/Fa rats) are treated dailyi for 10 days, by orally administering the compounds of the invention at a dose of 5 mg/kg/day in suspension in a solution containing 20% of Senegal gum. On the 11th day, the animals are sacrificed and blood is collected in order to determine glycemia, plasma triglycerides and immunoreactive insulin. Moreover, the animals are weighed before and after treatment.

Under these conditions, the compounds of the invention do not affect the level of glucose in circulation but decrease the level of plasma triglycerides as well as that of immunoreactive insulin. This activity is equal to or greater than that of other reference thiazolidinedione compounds.

PHARMACEUTICAL COMPOSITION

EXAMPLE 40

Tablet: preparation formula for 1,000 tablets containing 50 mg doses

| | |
|---|---|
| (−)-5-{4-[[1-(2-Benzothiazolyl)-(2S)-2-pyrrolidine]methoxy]benzyl}-2,4-thiazolidine-dione | 50 g |
| hydroxypropyl cellulose | 2 g |
| wheat starch | 10 g |
| lactose | 100 g |
| magnesium stearate | 3 g |
| talc | 3 g |

We claim:

1. A compound selected from those of formula (I),

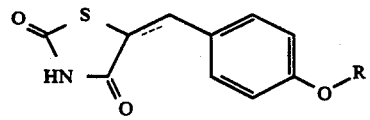

in which:
the dotted line indicates the optional presence of a double bond,
R represents the following group:

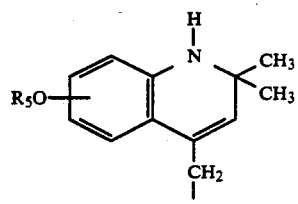

in which:
$R_5$ represents hydrogen or linear or branched ($C_1$-$C_6$)alkyl

2. A compound of claim 1, selected from those wherein R represents (1, 2-dihydro-2,2-dimethylquinol-4-yl)methyl, optionally substituted as in Formula H in claim 1, its enantiomers, and its addition salts with a pharmaceutically acceptable acid.

3. A compound of formula (I) as claimed in claim 1, which is 5-[4-[(6-ethoxy-1,2-dihydro -2,2-dimethyl-quinol-4-yl)methoxy]Benzyl]-2,4-thiazolidinedione and its addition salts with a pharmaceutically-acceptable acid.

4. A method for treating an animal or human living body afflicted with diabetes or obesity, comprising the step of administering to the living body an amount of a compound of claim 1 which is effective for alleviation of said conditions.

5. A pharmaceutical composition, useful for treating diabetes, or obesity, comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,296,605

DATED : March 22, 1994

INVENTOR(S) : Guillaume de Nanteuil, Jacques Duhault, Denis Ravel, and Yolande Herve It is certified that error appears in the above-indentified patent and that said Letters Patent is hereby corrected as shown below:

Col. 2, lines 30 to 35; Formula B should appear as follows:

Col. 4, line 18; "(V)", along the right margin, should read -- (IV) --.

Col. 4, line 29; move "(V)" down on the page so that it is located near the formula which it refers to in line 57.

Col. 5, line 2; delete the space between "i" and "s".

Col. 5, line 28; move "(VII)" down on the page so that it is located near the formula which it refers to in line 55.

Col. 7, line 2; move "(XIb)" down on the page so that it is located near the formula which it refers to in line 41, and change the layout of this page so that the CH3 of Formula (XIb) does not overlap with the N— of Formula (XIIIb) of Col. 8.

Col. 9, line 13; replace the semicolon at the end of this line with a colon.

Col. 11, line 25; "1100°" should read -- 110° --.

Col. 11, last line; insert the line -- specific rotation: $[\alpha]_D^{20}$ = - 141.7° (c = 10 mg/ml, DMSO) --.

Col. 12, line 4; "methoxylbezylidene)" should read -- methoxy]benxylidene} --.

Col. 12, line 21; "(4-([" should read -- {4-[[ --.

Col. 12, line 22; "methoxylbezylidene)" should read -- methoxy]benzylidene} --.

Col. 12, line 31; before "EXAMPLE 3" insert the line -- specific rotation: $[\alpha]_D^{20}$ = + 135.9° (c = 10 mg/ml, DMSO) --.

Col. 12, line 49; "[4" should read -- {4 --.

Col. 12, line 60; before "EXAMPLE 4" insert the line -- specific rotation: $[\alpha]_D^{20}$ = - 156.2° (c = 10 mg/ml, DMSO) --.

Col. 13, line 6; "benzylidenel-" should read -- benzylidene]- --

UNITED STATES PATENT AND TRADEMARK OFFICE
CERTIFICATE OF CORRECTION

PATENT NO. : 5,296,605
DATED : March 22, 1994
INVENTOR(S) : Guillaume de Nanteuil, Jacques Duhault, Denis Ravel, and Yolande Herve It is certified that error appears in the above-indentified patent and that said Letters Patent is hereby corrected as shown below:

Col. 13, line 58; "5-[4-4,5" should read -- 5-[4-[(4,5 --.
Col. 13, line 59; "methoxylbenzylidenel-" should read --methoxy]benzylidene] --.
Col. 14, line 20; "ethoxylbenzylidenel" should read -- ethoxy]benzylidene] --.
Col. 14, line 25; "1730°" should read -- 173° --.
Col. 14, line 37; "ethoxylbenzylidenel" should read -- ethoxy]benzylidene] --.
Col. 14, line 50; "5-(4" should read -- 5-[4 -- and delete the space between "Naphthy" and "l" and also between "et" and "hoxy".
Col. 14, line 52; "idene)-2 4" should read -- idene]-2,4 --.
Col. 14, line 55; replace the semicolon with a colon.
Col. 14, line 66; "ethoxylbenzylidenel" should read -- ethoxy]benzylidene] --.
Col. 15, lines 7 and 8; "ethoxylbenzylidenel" should read -- ethoxy]benzylidene] --.
Col. 15, line 14; "ethoxylben-" should read -- ethoxy]ben- --.
Col. 15, line 18; "5-(4" should read -- 5-{4 --.
Col. 15, line 19; "pyrrolidinyllmethoxylbenzylidenel" should read -- pyrrolidinyl]methoxy]benzylidene} --.
Col. 15, line 29; "5-(4" should read -- 5-{4 --.
Col. 15, line 30; "pyrrolidinyllmethoxylbenzylidene)" should read -- pyrrolidinyl]methoxy]benzylidene} --.
Col. 15, line 45; "thiazoyly" should read -- thiazolyl --.
Col. 15, lines 48 and 49; "pyrrolidinylloxylbenzylidenel" should read -- pyrrolidinyl]oxy]benzylidene] --.
Col. 15, lines 56 and 57; "oxylbenzylidenel" should read -- oxy]benzylidene] --.
Col. 15, line 61; "thylaminolethoxy]benzylidene]" should read -- thylamino]ethoxy]benzylidene} --.
Col. 15, lines 64 and 65; "pyrrolidinyllmethoxylbenzyl" should read -- pyrrolidinyl]methoxy]benzyl --.

UNITED STATES PATENT AND TRADEMARK OFFICE
CERTIFICATE OF CORRECTION

PATENT NO. : 5,296,605

DATED : March 22, 1994

Page 3 of 5

INVENTOR(S) Guillaume de Nanteuil, Jacques Duhault, Denis Ravel, and Yolande Herve It is certified that error appears in the above-indentified patent and that said Letters Patent is hereby corrected as shown below:

```
Col. 16, line 5; "950°" should read -- 95° --.
Col. 16, lines 18 and 19; "pyrrolidinyllmethoxylbenzyl)" should
      read -- pyrrolidinyl]methoxy]benzyl} --.
Col. 16, line 55; "methoxylbenzyl]" should read
      -- methoxy]benzyl] --.
Col. 17, line 19; "thoxylbenzyl" should read -- thoxy]benzyl --.
Col. 17, line 34; "12-(Naphthyl)ethoxylbenzyl]" should read
      -- [2-(Naphthyl)ethoxy]benzyl] --.
Col. 17, line 48; " ethoxylbenzyl]-" should read
      -- ethoxy]benzyl]- --.
Col. 18, line 3; "ethoxylbenzyll-" should read
      -- ethoxy]benzyl]- --.
Col. 18, line 12; "pyrrolidinyllmethoxylbenzyl}" should
      read -- pyrrolidinyl]methoxy]benzyl} --.
Col. 18, line 20; "5-f4" should read -- 5-{4 --.
Col. 18, line 21; "ylbenzyl)" should read -- y]benzyl} --.
Col. 18, line 27; "pyrrolidinylloxylbenzyl)-"should read
      -- pyrrolidinyl]oxy]benzyl}- --.
Col. 18, line 36; "thylaminolethoxylbenzyl)-" should read
      -- thylamino]ethoxy]benzyl}- --.
Col. 18, line 44; "thylaminocarbonyloxylbenzyll" should read
      -- thylaminocarbonyloxy]benzyl] --.
Col. 18, line 56; "Mm" should read -- mm --.
Col. 18, line 60; "thylaminocarbonyloxylbenzyll" should read
      -- thylaminocarbonyloxy]benzyl] --.
Col. 18, line 63; "methyll-" should read -- methyl]- --.
Col. 19, line 10; "methoxyl-" should read -- methoxy]- --.
Col. 19, line 11; "benzylidenej" should read -- benzylidene] --.
Col. 19, line 22; "methoxyl-" should read -- methoxy]- --.
Col. 19, line 23; "benzylidenel" should read -- benzylidene] --.
Col. 19, line 35; "benzylidenel" should read -- benzylidene] --.
Col. 19, line 47; "ylbenzylidenej" should read
      -- y]benzylidene] --.
```

UNITED STATES PATENT AND TRADEMARK OFFICE
CERTIFICATE OF CORRECTION

PATENT NO. : 5,296,605

DATED : March 22, 1994

INVENTOR(S) : Guillaume de Nanteuil, Jacques Duhault, Denis Ravel, and Yolande Herve It is certified that error appears in the above-indentified patent and that said Letters Patent is hereby corrected as shown below:

Col. 19, line 59; "methoxyl-" should read -- methoxy]- --.
Col. 19, line 60; "benzylj-" should read -- benzyl]- --.
Col. 20, line 13; "methoxylbenzyll" should read
 -- methoxy]benzyl] --.
Col. 20, line 31; "methoxylbenzyll" should read
 -- methoxy]benzyl] --.
Col. 20, line 46; "methoxylbenzylidenel" should read
 -- methoxy]benzylidene] --.
Col. 20, line 51; "methoxylbenzyll" should read
 -- methoxy]benzyl] --.
Col. 21, line 9; "yloxylbenzyll" should read -- yloxy]benzyl] --
Col. 21, line 12; "5-(4" should read -- 5-{4 --.
Col. 21, line 14; "methoxylbenzyl)" should read
 -- methoxy]benzyl} --.
Col. 21, line 68; "10°" should read -- 1° --.
Col. 23, line 31; "50C.," should read -- 5°C., --.
Col. 23, line 49; "methoxylbenzylj" should read
 -- methoxy]benzyl] --.
Col. 23, line 61; "methoxylbenzyll" should read
 -- methoxy]benzyl] --.
Col. 24, line 36; "5-14-1(2,3" should read -- 5-[4-[(2,3 --.
Col. 24, line 38; "yloxylbenzyl]" should read
 -- yloxy]benzyl] --.
Col. 24, line 54; "5-f4" should read -- 5-{4 --.
Col. 24, line 56; "zofuranyllmethoxylbenzyl)" should read
 -- zofuranyl]methoxy]benzyl} --.
Col. 25, line 17; insert -- invention -- before "have a".
Col. 25, line 54; "dailyi" should read -- daily, --.
Col. 26, line 30; delete "following" before "group:".
Col. 26, lines 31 to 40; insert -- (H) -- near the right margin to identify the formula.
Col. 26, line 48; insert a hyphen between "pharmaceutically" and "acceptable".

UNITED STATES PATENT AND TRADEMARK OFFICE
CERTIFICATE OF CORRECTION

PATENT NO. : 5,296,605
DATED : March 22, 1994
INVENTOR(S) : Guillaume de Nanteuil, Jacques Duhault, Denis Ravel, and Yolande Herve It is certified that error appears in the above-indentified patent and that said Letters Patent is hereby corrected as shown below:

Col. 26, line 49; delete "formula (I) as claimed in".
Col. 26, line 50; delete "which is" and insert -- selected from -- before "5-[4-[(6".
Col. 26, line 51; "Benzyl" should read -- benzyl --.
Col. 26, line 60; delete the comma after "diabetes".

Signed and Sealed this

Thirteenth Day of September, 1994

Attest:

BRUCE LEHMAN

Attesting Officer

Commissioner of Patents and Trademarks